(12) United States Patent
Ford et al.

(10) Patent No.: US 8,455,657 B2
(45) Date of Patent: Jun. 4, 2013

(54) PROCESS FOR THE PREPARATION OF 3-ALKYLSULFINYLBENZOYL DERIVATIVES

(75) Inventors: Mark James Ford, Schmitten (DE); Jan Peter Schmidt, Hofheim (DE); Helmut Kohlhepp, Moerfelden-Walldorf (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 13/335,662

(22) Filed: Dec. 22, 2011

(65) Prior Publication Data
US 2012/0165540 A1 Jun. 28, 2012

(30) Foreign Application Priority Data

Dec. 28, 2010 (EP) .................................... 10197151

(51) Int. Cl.
*C07D 271/08* (2006.01)
*C07D 271/10* (2006.01)
*C07D 271/00* (2006.01)
*C07D 257/04* (2006.01)
*C07D 249/00* (2006.01)
*C07D 231/10* (2006.01)
*C07C 319/00* (2006.01)

(52) U.S. Cl.
USPC ........ 548/125; 548/143; 548/251; 548/265.4; 548/396.4; 568/37

(58) Field of Classification Search
USPC ........ 548/125, 134, 251, 265.4, 369.4; 568/37
See application file for complete search history.

(56) References Cited

U.S. PATENT DOCUMENTS

| | | | |
|---|---|---|---|
| 6,004,903 | A | 12/1999 | von Dehn et al. |
| 7,932,211 | B2 | 4/2011 | Ahrens et al. |
| 7,943,551 | B2 | 5/2011 | Aherns et al. |
| 2005/0282709 | A1 | 12/2005 | van Almsick et al. |
| 2008/0305956 | A1 | 12/2008 | Ahrens et al. |
| 2010/0004129 | A1 | 1/2010 | Aherns et al. |
| 2011/0045980 | A1 | 2/2011 | Aherns et al. |
| 2011/0053779 | A1 | 3/2011 | Aherns et al. |
| 2011/0152534 | A1 | 6/2011 | Lui et al. |

FOREIGN PATENT DOCUMENTS

| | | |
|---|---|---|
| EP | 2 127 521 | 12/2009 |
| WO | 96/26200 | 8/1996 |
| WO | 2005/122768 | 12/2005 |
| WO | 2008/125214 | 10/2008 |
| WO | 2008/151719 | 12/2008 |
| WO | 2009/149806 | 12/2009 |
| WO | 2010/035874 | 4/2010 |
| WO | 2011/012246 | 2/2011 |
| WO | 2011/012247 | 2/2011 |

OTHER PUBLICATIONS

International Search Report for PCT/EP2011/073906 maild Apr. 5, 2012.

*Primary Examiner* — Samantha Shterengarts
(74) *Attorney, Agent, or Firm* — Baker Donelson Bearman Caldwell & Berkowitz, PC

(57) ABSTRACT

A process is described for the preparation of 3-alkylsulfinyl-benzoyl derivatives of the formula (IIIa) by reaction of 3-alkylsulfinylbenzoic acids of the formula (Ib) with compounds of the formula (II) in the presence of a chlorinating agent and a base.

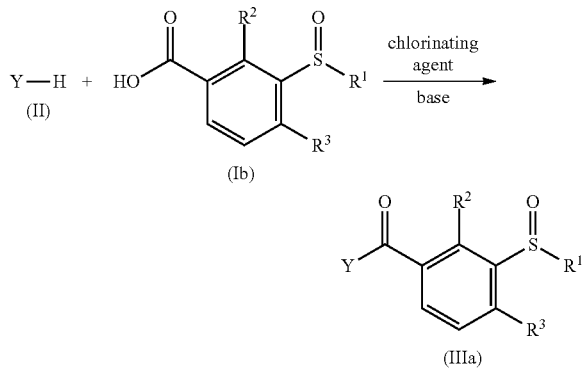

In the formulae specified above, Y is a radical such as pyrazolyl and cyclohexanedionyl. $R^1$, $R^2$ and $R^3$ are radicals such as halogen, nitro, cyano and alkyl.

13 Claims, No Drawings

PROCESS FOR THE PREPARATION OF 3-ALKYLSULFINYLBENZOYL DERIVATIVES

CROSS REFERENCE TO RELATED APPLICATIONS

This application claims priority to EP 10197151.3 filed Dec. 28, 2010, the content of which is incorporated herein by reference in its entirety.

BACKGROUND

1. Field of the Invention

The invention relates to the technical field of the preparation of crop protection agents.

2. Description of Related Art

It is already known from various publications that certain 3-alkylsulfinylbenzoyl derivatives have herbicidal properties. For example, in each of EP 2 167 473 A1, EP 2 127 521 A1, WO 2008/125214 A1, WO 2009/149806 A1 and WO 2011/012246 A1, 3-alkylsulfinylbenzoylpyrazoles are described as herbicides. In WO 2011/012247 A1, in each case 3-alkylsulfinylbenzoylcyclohexanediones are described as herbicides. WO 2011/035874 A1 describes N-(1,2,5-oxadiazol-3-yl) benzamides which carry, inter alia, a 3-alkylsulfinyl group in the 3 position of the phenyl ring. The preparation processes specified in these documents relate, for example, to a condensation process shown in scheme 1, in which a 3-alkylsulfinyl-benzoic acid of the formula (I) is reacted with a compound of the formula (II) in the presence of a water-withdrawing agent, such as N-(3-dimethylaminopropyl)-$N^1$-ethylcarbodiimide hydrochloride (EDCI), and optionally a cyanide to give the desired 3-alkylsulfinyl-benzoyl derivate of the formula (III).

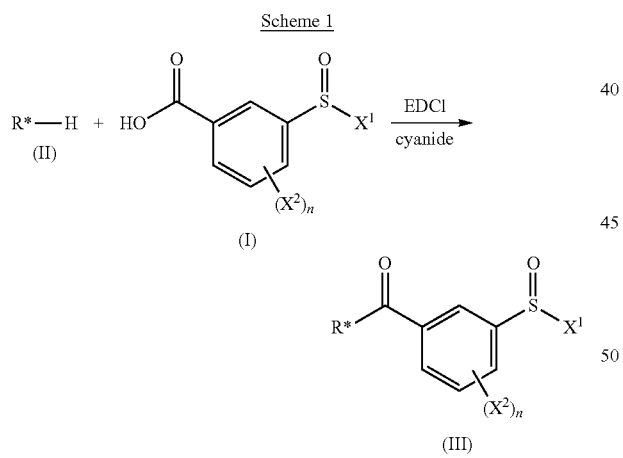

In said scheme, the radicals have the following meanings: $X^1$ is alkyl, $X^2$ is various radicals, R*—H is in each case an optionally substituted 5-hydroxypyrazole or cyclohexanedione, n is 0, 1 or 2.

Furthermore, in some of the aforementioned documents, a preparation process as shown in scheme 2 is mentioned, in which, in a first step, the 3-alkylsulfinylbenzoic acid of the formula (I) is reacted with, for example, thionyl chloride to give the 3-alkylsulfinylbenzoic acid chloride of the formula (Ia) and this is then reacted with a compound of the formula (II) in the presence of a base and a cyanide to give the desired 3-alkylsulfinylbenzoyl derivative of the formula (III).

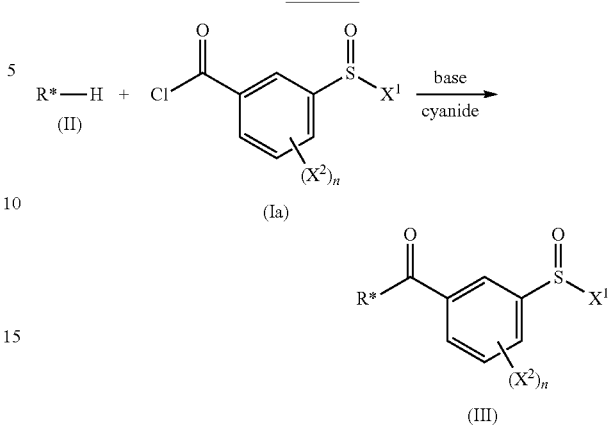

However, the processes known from these documents have a number of disadvantages. For example, in the process according to scheme 1, very expensive and toxic water-withdrawing agents are used. Since these agents are used not in catalytic amounts, but in equimolar amounts, moreover, large amounts of waste products are formed. The process shown in scheme 2 has the disadvantage that it only leads to a low yield of the desired 3-alkylsulfinylbenzoyl derivative of the formula (III). The factor responsible for the low yield is the lack of chemical stability, known to the person skilled in the art, of the 3-alkylsulfinylbenzoic acid chlorides of the formula (Ia), which are very quickly reduced to the corresponding 3-alkyl-sulfenyl-benzoyl derivatives. Furthermore, it is known, for example from "Nachrichten aus der Chemie, Technik and Laboratorium", 1983, 31, 11, 892-896, that when attempting to prepare compounds of the formula (Ia) with the help of chlorinating agents, the chlorinating agent usually produces an unstable sulfinium chloride (Q), which does not lead to the desired product (III), but leads, in a Pummerer rearrangement, to the compound of the formula (W) (scheme 2b).

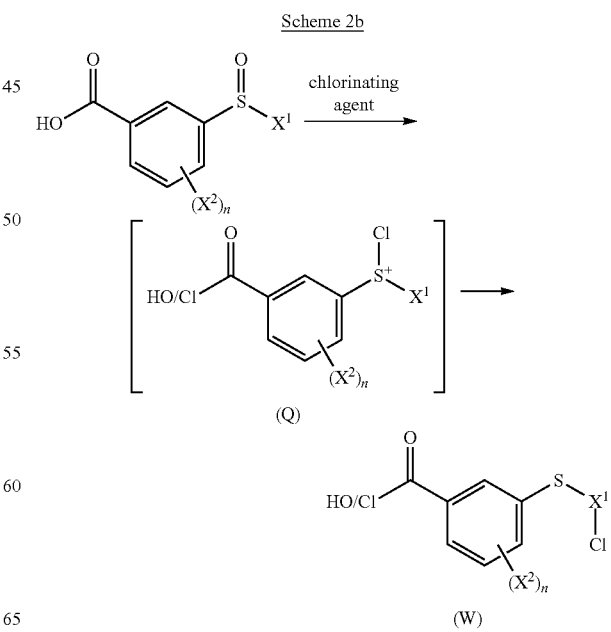

SUMMARY

The object of the present invention is to provide a process for the preparation of 3-alkylsulfinylbenzoyl derivatives which overcomes the disadvantages of the processes known from the prior art.

It has now been found that certain 3-alkylsulfinylbenzoyl derivatives can be prepared in a cost-effective manner and in high yields by reaction of 3-alkylsulfinylbenzoic acids and compounds from the group consisting of in each case unsubstituted or substituted 5-hydroxypyrazoles, cyclohexanediones, 4-amino-1,2,5-oxadiazoles, 5-amino-1H-1,2,4-triazoles and 5-amino-1H-tetrazoles in the presence of a chlorinating agent, a base and optionally a cyanide source.

The present invention thus provides a process for the preparation of 3-alkylsulfinylbenzoyl derivatives of the formula (IIIa) by reaction of 3-alkylsulfinylbenzoic acids of the formula (Ib) with compounds of the formula (II) in the presence of a chlorinating agent and a base

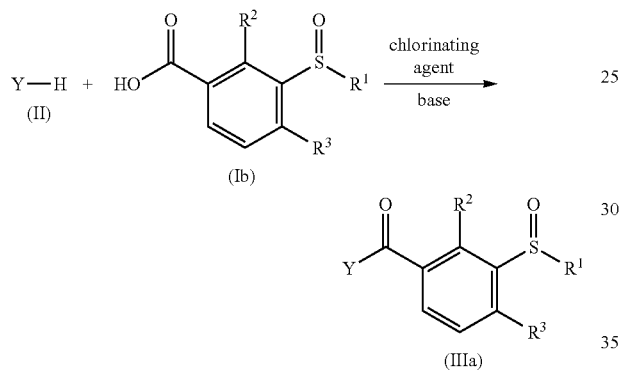

in which the radicals, symbols and indices have the following meanings:

$R^1$ is $(C_1-C_8)$-alkyl, $(C_3-C_8)$-cycloalkyl or benzyl substituted in each case by s radicals from the group consisting of halogen, $(C_1-C_2)$-alkoxy and halo-$(C_1-C_2)$-alkyl, $R^2$ is hydrogen, mercapto, nitro, halogen, cyano, rhodano, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $OR^4$, $OCOR^4$, $OSO_2R^4$, $S(O)_nR^4$, $SO_2OR^4$, $SO_2N(R^4)_2$, $NR^4SO_2R^4$, $NR^4COR^4$, $(C_1-C_6)$-alkyl-$S(O)_nR^4$, $(C_1-C_6)$-alkyl-$OR^4$, $(C_1-C_6)$-alkyl-$OCOR^4$, $(C_1-C_6)$-alkyl-$OSO_2R^4$, $(C_1-C_6)$-alkyl-$SO_2OR^4$, $(C_1-C_6)$-alkyl-$SO_2N(R^4)_2$ or $(C_1-C_6)$-alkyl-$NR^4COR^4$, $R^3$ is fluorine, chlorine, bromine, iodine, nitro, $CF_3$ or the group $SO_2R$, $R^4$ is hydrogen, $(C_1-C_6)$-alkyl, $(C_2-C_6)$-alkenyl, $(C_2-C_6)$-alkynyl, $(C_3-C_6)$-cycloalkyl, phenyl or phenyl-$(C_1-C_6)$-alkyl, where the six last-mentioned radicals are substituted by s radicals of the group hydroxy, mercapto, amino, cyano, nitro, rhodano, $OR^5$, $SR^5$, $N(R^5)_2$, $NOR^5$, $OCOR^5$, $SCOR^5$, $NR^5COR^5$, $CO_2R^5$, $COSR^5$, $CON(R^5)_2$, $(C_1-C_4)$-alkyliminooxy, $(C_1-C_4)$-alkylcarbonyl, $(C_1-C_4)$-alkoxy-$(C_2-C_6)$-alkoxycarbonyl and $(C_1-C_4)$-alkylsulfonyl, $R^5$ is hydrogen, $(C_1-C_6)$-alkyl, $(C_2-C_6)$-alkenyl or $(C_2-C_6)$-alkynyl, R is $(C_1-C_4)$-alkyl, n is 0, 1 or 2, s is 0, 1, 2 or 3, Y is a radical Y1, Y2, Y3, Y4, Y5 or Y6:

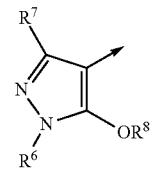

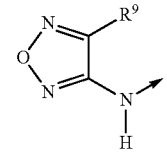

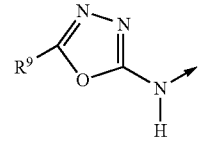

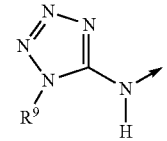

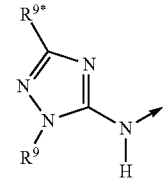

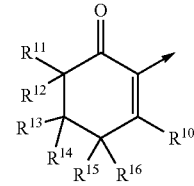

$R^6$ is $(C_1-C_4)$-alkyl, $R^7$ is hydrogen or $(C_1-C_4)$-alkyl, $R^8$ is hydrogen, $(C_1-C_6)$-alkylsulfonyl, $(C_1-C_4)$-alkoxy-$(C_1-C_6)$-alkylsulfonyl, or phenylsulfonyl, thiophenyl-2-sulfonyl, benzoyl, benzoyl-$(C_1-C_6)$-alkyl or benzyl substituted in each case by s radicals from the group consisting of halogen, $(C_1-C_4)$-alkyl and $(C_1-C_4)$-alkoxy, $R^9$ is hydrogen, $(C_1-C_6)$-alkyl, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $CH_2R^{18}$ or phenyl substituted by s radicals from the group halogen, nitro, cyano, $(C_1-C_6)$-alkyl, halo-$(C_1-C_6)$-alkyl, $(C_3-C_6)$-cycloalkyl, $S(O)_n-(C_1-C_6)$-alkyl, $(C_1-C_6)$-alkoxy, halo-$(C_1-C_6)$-alkoxy, $(C_1-C_6)$-alkoxy-$(C_1-C_4)$-alkyl, $R^{9*}$ is hydrogen, nitro, halogen, cyano, rhodano, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the last 6 radicals are substituted in each case by s radicals from the group halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries 0 to 2 oxo groups, $R^{19}$ is hydroxy or $SR^{17}$, $R^{11}$ and $R^{16}$, independently of one another, are hydrogen or $(C_1-C_4)$-alkyl, or the radicals $R^{11}$ and $R^{16}$ together form the unit Z, which is an oxygen atom or a sulfur atom or one to four methylene groups, $R^{12}$ and $R^{15}$, independently of one another, are hydrogen or $(C_1-C_4)$-alkyl, $R^{13}$ and $R^{14}$, independently of one another, are hydrogen or $(C_1-C_4)$-alkyl or, together with the carbon atom to which they are bonded, form a carbonyl group, $R^{17}$ is $(C_1-C_4)$-alkyl, phenyl substituted by s radicals from the group consisting of nitro, cyano, $(C_1-C_4)$-alkyl, $(C_1-C_4)$-haloalkyl, $(C_1-C_4)$-alkoxy and $(C_1-C_4)$-haloalkoxy, or partially or completely halogenated phenyl, $R^{18}$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy, $(C_3-C_6)$-cycloalkyl or phenyl substituted by s radicals from the group methyl, ethyl, methoxy, trifluoromethyl and halogen.

In the aforementioned radicals Y1 to Y6, the arrow in each case means the linkage to the remainder of the molecule.

DETAILED DESCRIPTION OF A PREFERRED EMBODIMENT

The compounds of the formula (IIIa) which can be prepared by the process according to the invention thus have, depending on the meaning of the radical Y, the structures of the formulae (IIIa1), (IIIa2), (IIIa3), (IIIa4), (IIIa5) and (IIIa6):

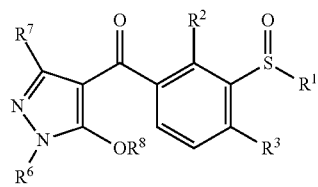
(IIIa1)

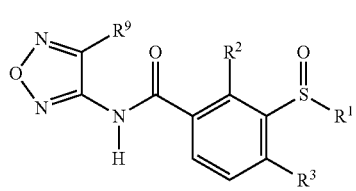
(IIIa2)

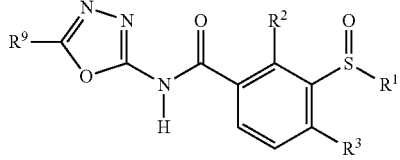
(IIIa3)

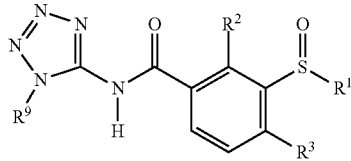
(IIIa4)

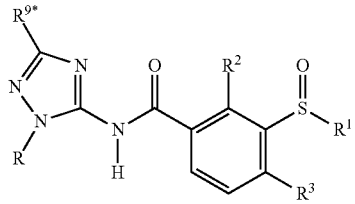
(IIIa5)

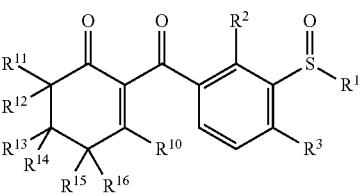
(IIIa6)

A particular advantage of the process according to the invention is also the fact that it can be carried out in a single-stage reaction without further intermediates having to be isolated.

A further advantage of the process according to the invention is also the fact that the stereochemical information of the compounds of the formula (Ib) is not lost during the reaction to give the compounds of the formula (IIIa), i.e. no racemization takes place, especially not on the sulfinyl group $S(=O)R^1$.

In the formula (I) and all of the subsequent formulae, alkyl radicals with more than two carbon atoms can be straight-chain or branched. Alkyl radicals are e.g. methyl, ethyl, n-propyl or isopropyl, n-butyl, isobutyl, t-butyl or 2-butyl, pentyls, hexyls, such as n-hexyl, isohexyl and 1,3-dimethyl-butyl. Halogen is fluorine, chlorine, bromine or iodine. Tosyl is 4-methylphenylsulfonyl.

Heterocyclyl is a saturated, partially saturated or completely unsaturated cyclic radical which contains 3 to 6 ring atoms, of which 1 to 4 originate from the group oxygen, nitrogen and sulfur, and which can additionally be fused by a benzo ring. For example, heterocyclyl is piperidinyl, pyrrolidinyl, tetrahydrofuranyl, dihydrofuranyl and oxetanyl, Heteroaryl is an aromatic cyclic radical which contains 3 to 6 ring atoms, of which 1 to 4 originate from the group oxygen, nitrogen and sulfur, and which can additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3, 4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is substituted two or more times by radicals, then this is to be understood as meaning that this group is substituted by one or more identical or different radicals specified.

In all of the formulae given below, the substituents, symbols and indices, unless defined otherwise, have the same meaning as described under the aforementioned formulae (Ib), (II), (IIIa), (IIIa1), (IIIa2), (IIIa3), (IIIa4), (IIIa5), Y1, Y2, Y3, Y4 and Y5.

In the process according to the invention, the radicals, symbols and indices preferably have the following meaning:

$R^1$ is $(C_1-C_4)$-alkyl, $R^2$ is nitro, halogen, $(C_1-C_4)$-alkyl, trifluoromethyl, $(C_1-C_4)$-alkoxy, methylsulfonyl, methoxymethyl, methoxymethoxymethyl, ethoxyethoxymethyl, ethoxymethoxymethyl, methoxyethoxymethyl, methoxypropoxymethyl, methylsulfonylmethyl, methylsulfonylethoxymethyl, methoxyethylsulfonylmethyl, methylsulfonylethylsulfonylmethyl, $R^3$ is fluorine, chlorine, bromine, iodine, $CF_3$ or the group $SO_2R$, Y is a radical Y1, Y2, Y3, Y4, Y5 or Y6:

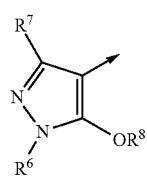
Y1

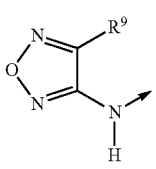
Y2

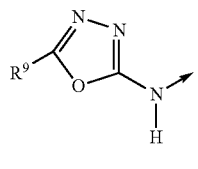
Y3

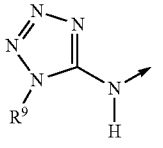
Y4

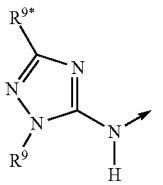
Y5

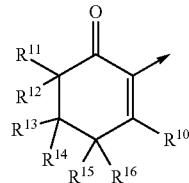
Y6

$R^6$ is methyl, ethyl, n-propyl or isopropyl, $R^7$ is hydrogen, methyl, ethyl, n-propyl or isopropyl, $R^8$ is hydrogen, $(C_1-C_3)$-alkylsulfonyl, $(C_1-C_2)$-alkoxy-$(C_1-C_4)$-alkylsulfonyl, or phenylsulfonyl, thiophenyl-2-sulfonyl, benzoyl, benzoyl-$(C_1-C_6)$-alkyl or benzyl substituted in each case by s methyl groups, s is 0, 1, 2 or 3, $R^9$ is $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, or phenyl or benzyl substituted by s radicals from the group methyl, methoxy, trifluoromethyl and halogen, $R^{9*}$ is hydrogen, $(C_1-C_6)$-alkyl, halo-$(C_1-C_6)$-alkyl, $(C_3-C_6)$-cycloalkyl, $COR^1$, $OR^1$, $COOR^1$ or $(C_1-C_6)$-alkylphenyl, $R^{10}$ is hydroxy, $R^{11}$ and $R^{16}$, independently of one another, are hydrogen or $(C_1-C_4)$-alkyl, or the radicals $R^{11}$ and $R^{16}$ together form a methylene group or ethylene group, $R^{12}$ and $R^{15}$, independently of one another, are hydrogen, methyl or ethyl, $R^{13}$ and $R^{14}$, independently of one another, are hydrogen, methyl or ethyl.

The process according to the invention is generally carried out such that the compounds of the formulae (Ib) and (II) are reacted in an organic solvent with a chlorinating agent in the presence of a base. Depending on the reactivity of the compounds of the formulae (Ib) and (II), it may be expedient to carry out the process according to the invention also in the presence of a cyanide source.

The process according to the invention can be carried out in a wide temperature range, depending on the reactivity of the reactants used. Usually, it is carried out at a temperature of from −100 to −5° C., preferably at a temperature of from −80 to −15° C., particularly preferably at a temperature of from −50 to −20° C.

Suitable chlorinating agents are thionyl chloride, phosphorus oxychloride, oxalyl chloride and phosgene. Preferred chlorinating agents are thionyl chloride and phosgene. A particularly preferred chlorinating agent is thionyl chloride.

The bases used are usually weak bases, i.e. those with a $pK_B$ value greater than 4.75. Preferred bases are organic amines. Particularly preferred bases are pyridine, alkylpyridines such as 3-methylpyridine and dialkylpyridines such as 3,5-dimethyl-pyridine or 2-methyl-5-ethylpyridine.

Suitable solvents are aprotic and dipolar aprotic solvents, such as alkanoic acid alkyl esters, chloroalkanes, chloroaromatics, chloralkylaromatics, alkylnitriles and arylnitriles. Preferred solvents are ethyl acetate, propyl acetate, isopropyl acetate, butyl acetate, dichloromethane, dichloroethane, chlorotoluene, acetonitrile, butyronitrile and benzonitrile. Particularly preferred solvents are ethyl acetate, dichloromethane and dichloroethane.

The cyanide source used is usually cyanide compounds which are able to cleave off cyanide in the aforementioned solvents. Preferred cyanide sources are acetone cyanohydrin and alkali metal cyanides, such as potassium cyanide and sodium cyanide. A particularly preferred cyanide source is acetone cyanohydrin.

In the process according to the invention, the coompouds of the formulae (Ib) and (II) are usually used in a stoichiometric ratio. The chlorinating agent is usually used in a ratio of from 1:1 to 1.5:1 relative to the compound of the formula (Ib). The base is usually used in a ratio of from 1:1 to 6:1, relative to the compound of the formula (Ib). The cyanide source, if required, is usually used in catalytic amounts, i.e. with about 1 to 10 mol % based on compound of the formula (Ib).

As a rule, the process according to the invention proceeds rapidly and in high yields, even at low temperatures. The examples below illustrate the process according to the invention in more detail.

1a. Preparation of (5-hydroxy-1-methyl-1H-pyrazol-4-yl)[2-methoxy-3-(methylsulfinyl)-4-(trifluoromethyl)phenyl]methanone 3.0 g of 2-methoxy-3-methylsulfinyl-4-trifluoromethylbenzoic acid and 1.02 g of 3-hydroxy-2-methylpyrazole are suspended in 30 ml of ethyl acetate and 4.21 ml of pyridine under an inert atmosphere and cooled to −20° C. with stirring. 1.24 g of thionyl chloride are then slowly added dropwise such that the temperature always remains below −15° C. Following the complete addition of the thionyl chloride, the mixture is stirred for a further 20 minutes and warmed to −10° C. 10 ml of cold water are then added, and the mixture is warmed to 0° C. After adding 40 ml of heptane, the suspension is filtered and washed with 20 ml of heptane, 10 ml of water and again with 20 ml of heptane. Drying gives 3.32 g of (5-hydroxy-1-methyl-1H-pyrazol-4-yl)[2-methoxy-3-(methylsulfinyl)-4-(trifluoromethyl)phenyl]methanone (84% yield).

1b. Preparation of (5-hydroxy-1-methyl-1H-pyrazol-4-yl)[2-methoxy-3-(methylsulfinyl)-4-(trifluoromethyl)phenyl]methanone 3.0 g of 2-methoxy-3-methylsulfinyl-4-trifluoromethylbenzoic acid and 1.02 g of 3-hydroxy-2-methylpyrazole are suspended in 20 ml of ethyl acetate and 5.07 ml of 3-methylpyridine under an inert atmosphere and cooled to −25° C. with stirring. 1.24 g of thionyl chloride are then slowly added dropwise such that the temperature always remains below −20° C. Following the complete addition of the thionyl chloride, the mixture is stirred for a further 20 minutes. 40 µl of cold water and 20 ml of methylcyclohexane are then added. The mixture is then stirred for a further 20 minutes at −25° C. The suspension is filtered and washed once with 10 ml of methylcyclohexane and twice with 10 ml of water in each case. Drying gives 3.67 g of (5-hydroxy-1-methyl-1H-pyrazol-4-yl)[2-methoxy-3-(methylsulfinyl)-4-(trifluoromethyl)phenyl]methanone (86.5% yield).

2. Preparation of [3-(ethylsulfinyl)-2-methyl-4-(methylsulfonyl)phenyl](5-hydroxy-1-methyl-1H-pyrazol-4-yl)methanone 305 mg of 2-methyl-3-ethylsulfinyl-4-methylsulfonylbenzoic acid and 106 mg of 3-hydroxy-2-methylpyrazole are suspended in 2 ml of ethyl acetate and 407 mg of pyridine under an inert atmosphere and cooled to −25° C. with stirring. 129 mg of thionyl chloride are then slowly added dropwise such that the temperature always remains below −20° C. Following the complete addition of the thionyl chloride, the mixture is stirred for a further 20 minutes. A further 27 mg of 3-hydroxy-2-methylpyrazole are added, and 42 mg of thionyl chloride are slowly added dropwise such that the temperature always remains below −25° C. 4 µl of cold water are then added and the mixture is warmed to 0° C. After separating the organic phase from the aqueous phase, the aqueous phase is extracted twice with 5 ml of ethyl acetate in each case. The combined organic phases are dried, giving 370 mg of [3-(ethylsulfinyl)-2-methyl-4-(methylsulfonyl)phenyl](5-hydroxy-1-methyl-1H-pyrazol-4-yl)methanone (91% yield).

3. Preparation of (5-hydroxy-1-methyl-1H-pyrazol-4-yl)[2-methyl-3-(methyl-sulfinyl)-4-(trifluoromethyl)phenyl]methanone 3.0 g of 2-methyl-3-methylsulfinyl-4-trifluoromethylbenzoic acid and 1.25 g of 3-hydroxy-2-methylpyrazole are suspended in 20 ml of ethyl acetate and 4.8 g of pyridine under an inert atmosphere and cooled to −25° C. with stirring. 1.51 g of thionyl chloride are then slowly added dropwise such that the temperature always remains below −20° C. Following the complete addition of the thionyl chloride, the mixture is stirred for a further 20 minutes. 40 µl of cold water, 10 ml of ethyl acetate and a further 10 ml of water are added, and the mixture is heated to 0° C. After separating the organic phase from the aqueous phase, the aqueous phase is extracted twice with 5 ml of ethyl acetate in each case. The combined organic phases are dried, giving 3.69 g of (5-hydroxy-1-methyl-1H-pyrazol-4-yl)[2-methyl-3-(methylsulfinyl)-4-(trifluoromethyl)phenyl]methanone (90.7% yield).

4. Preparation of 3-[2-methoxy-3-(methylsulfinyl)-4-(trifluoromethyl)benzoyloxy]cyclohex-2-en-1-one 3.0 g of 2-methoxy-3-methylsulfinyl-4-trifluoromethylbenzoic acid and 1.68 g of 1,3-cyclohexanedione are suspended in 20 ml of ethyl acetate and 5.61 ml of pyridine under an inert atmosphere and cooled to −25° C. with stirring. 1.73 g of thionyl chloride are then slowly added dropwise such that the temperature always remains below −20° C. Following the complete addition of the thionyl chloride, the mixture is stirred for a further 20 minutes. 38 µl of cold water are added, and the mixture is warmed to 0° C. 10 ml of ethyl acetate and a further 10 ml of water are then added. After separating the organic phase from the aqueous phase, the aqueous phase is extracted twice with 5 ml of ethyl acetate in each case. The combined organic phases are dried, giving 3.57 g of 3-[2-methoxy-3-(methylsulfinyl)-4-(trifluoro-methyl)benzoyloxy]cyclohex-2-en-1-one (85.5% yield).

The invention claimed is:
1. A process for preparing a 3-alkylsulfinylbenzoyl derivative of formula (IIIa) comprising a reaction of a 3-alkylsulfinylbenzoic acid of formula (Ib) with a compound of formula (II) in the presence of a chlorinating agent and a base selected from the group consisting of pyridine, 3-methylpyridine, and 3,5-dimethylpyridine

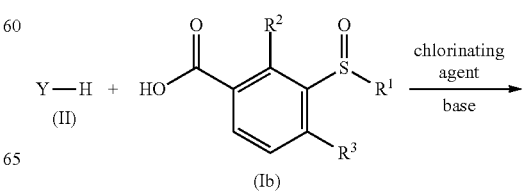

-continued

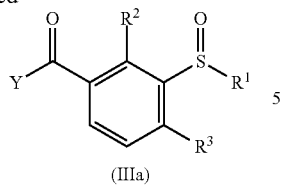

(IIIa)

in which the radicals, symbols and indices have the following meanings:

$R^1$ is $(C_1-C_8)$-alkyl, $(C_3-C_8)$-cycloalkyl or benzyl substituted in each case by s radicals selected from the group consisting of halogen, $(C_1-C_2)$-alkoxy and halo-$(C_1-C_2)$-alkyl, $R^2$ is hydrogen, mercapto, nitro, halogen, cyano, rhodano, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $OR^4$, $OCOR^4$, $OSO_2R^4$, $S(O)_nR^4$, $SO_2OR^4$, $SO_2N(R^4)_2$, $NR^4SO_2R^4$, $NR^4COR^4$, $(C_1-C_6)$-alkyl-$S(O)_nR^4$, $(C_1-C_6)$-alkyl-$OR^4$, $(C_1-C_6)$-alkyl-$OCOR^4$, $(C_1-C_6)$-alkyl-$OSO_2R^4$, $(C_1-C_6)$-alkyl-$SO_2OR^4$, $(C_1-C_6)$-alkyl-$SO_2N(R^4)_2$ or $(C_1-C_6)$-alkyl-$NR^4COR^4$, $R^3$ is fluorine, chlorine, bromine, iodine, nitro, $CF_3$ or the group $SO_2R$, $R^4$ is hydrogen, $(C_1-C_6)$-alkyl, $(C_2-C_6)$-alkenyl, $(C_2-C_6)$-alkynyl, $(C_3-C_6)$-cycloalkyl, phenyl or phenyl-$(C_1-C_6)$-alkyl, where the six last-mentioned radicals are substituted by s radicals of the group hydroxy, mercapto, amino, cyano, nitro, rhodano, $OR^5$, $SR^5$, $N(R^5)_2$, $NOR^5$, $OCOR^5$, $SCOR^5$, $NR^5COR^5$, $CO_2R^5$, $COSR^5$, $CON(R^5)_2$, $(C_1-C_4)$-alkyliminooxy, $(C_1-C_4)$-alkylcarbonyl, $(C_1-C_4)$-alkoxy-$(C_2-C_6)$-alkoxycarbonyl and $(C_1-C_4)$-alkylsulfonyl, $R^5$ is hydrogen, $(C_1-C_6)$-alkyl, $(C_2-C_6)$-alkenyl or $(C_2-C_6)$-alkynyl, R is $(C_1-C_4)$-alkyl, n is 0, 1 or 2, s is 0, 1, 2 or 3, Y is a radical Y1, Y2, Y3, Y4, Y5 or Y6:

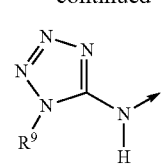
Y1

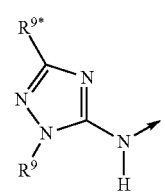
Y2

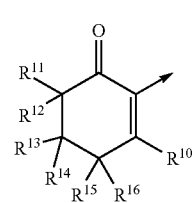
Y3

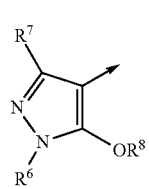
Y4

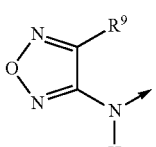
Y5

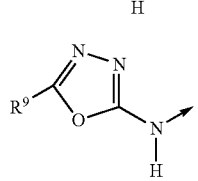
Y6

$R^6$ is $(C_1-C_4)$-alkyl, $R^7$ is hydrogen or $(C_1-C_4)$-alkyl, $R^8$ is hydrogen, $(C_1-C_6)$-alkylsulfonyl, $(C_1-C_4)$-alkoxy-$(C_1-C_6)$-alkylsulfonyl, or phenylsulfonyl, thiophenyl-2-sulfonyl, benzoyl, benzoyl-$(C_1-C_6)$-alkyl or benzyl substituted in each case by s radicals selected from the group consisting of halogen, $(C_1-C_4)$-alkyl and $(C_1-C_4)$-alkoxy, $R^9$ is hydrogen, $(C_1-C_6)$-alkyl, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $CH_2R^{18}$ or phenyl substituted by s radicals from the group halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl, $R^{9*}$ is hydrogen, nitro, halogen, cyano, rhodano, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$CN$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the last 6 radicals are substituted in each case by s radicals from the group halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries 0 to 2 oxo groups, $R^{10}$ is hydroxy or $SR^{17}$, $R^{11}$ and $R^{16}$, independently of one another, are hydrogen or $(C_1-C_4)$-alkyl, or the radicals $R^{11}$ and $R^{16}$ together form the unit Z, which is an oxygen atom or a sulfur atom or one to four methylene groups, $R^{12}$ and $R^{15}$, independently of one another, are hydrogen or $(C_1-C_4)$-alkyl, $R^{13}$ and $R^{14}$, independently of one another, are hydrogen or $(C_1-C_4)$-alkyl or, together with the carbon atom to which they are bonded, form a carbonyl group, $R^{17}$ is $(C_1-C_4)$-alkyl, phenyl substituted by s radicals from the group consisting of nitro, cyano, $(C_1-C_4)$-alkyl, $(C_1-C_4)$-haloalkyl, $(C_1-C_4)$-alkoxy and $(C_1-C_4)$-haloalkoxy, or partially or completely halogenated phenyl, $R^{18}$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy, $(C_3-C_6)$-cycloalkyl or phenyl substituted by s radicals from the group methyl, ethyl, methoxy, trifluoromethyl and halogen.

2. The process as claimed in claim 1, in which the radicals, symbols and indices have the following meanings:

$R^1$ is $(C_1-C_4)$-alkyl, $R^2$ is nitro, halogen, $(C_1-C_4)$-alkyl, trifluoromethyl, $(C_1-C_4)$-alkoxy, methylsulfonyl, methoxymethyl, methoxymethoxymethyl, ethoxyethoxymethyl, ethoxymethoxymethyl, methoxyethoxymethyl, methoxypropoxymethyl, methylsulfonylmethyl, methylsulfonylethoxymethyl, methoxyethylsulfonylmethyl, methylsulfonylethylsulfonylmethyl, $R^3$ is fluorine, chlorine, bromine, iodine, $CF_3$ or the group $SO_2R$, Y is a radical Y1, Y2, Y3, Y4, Y5 or Y6:

$R^6$ is methyl, ethyl, n-propyl or isopropyl, $R^7$ is hydrogen, methyl, ethyl, n-propyl or isopropyl, $R^8$ is hydrogen, $(C_1-C_3)$-alkylsulfonyl, $(C_1-C_2)$-alkoxy-$(C_1-C_4)$-alkylsulfonyl, or phenylsulfonyl, thiophenyl-2-sulfonyl, benzoyl, benzoyl-$(C_1-C_6)$-alkyl or benzyl substituted in each case by s methyl groups, s is 0, 1, 2 or 3, $R^9$ is $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, or phenyl or benzyl substituted by s radicals from the group methyl, methoxy, trifluoromethyl and halogen, $R^{9*}$ is hydrogen, $(C_1-C_6)$-alkyl, halo-$(C_1-C_6)$-alkyl, $(C_3-C_6)$-cycloalkyl, $COR^1$, $OR^1$, $COOR^1$ or $(C_1-C_6)$-alkylphenyl, $R^{10}$ is hydroxy, $R^{11}$ and $R^{16}$, independently of one another, are hydrogen or $(C_1-C_4)$-alkyl, or the radicals $R^{11}$ and $R^{16}$ together form a methylene group or ethylene group, $R^{12}$ and $R^{15}$, independently of one another, are hydrogen, methyl or ethyl, $R^{13}$ and $R^{14}$, independently of one another, are hydrogen, methyl or ethyl.

3. The process as claimed in claim 1, where the reaction is carried out at a temperature of from −80 to −15° C.

4. The process as claimed in claim 1, where the reaction is carried out at a temperature of from −50 to −20° C.

5. The process as claimed in claim 1, where the chlorinating agent is selected from the group consisting of thionyl chloride, phosphorus oxychloride, oxalyl chloride and phosgene.

6. The process as claimed in claim 1, where the chlorinating agent is selected from the group consisting of thionyl chloride and phosgene.

7. The process as claimed in claim 1, where the chlorinating agent is thionyl chloride.

8. The process of claim 1, wherein the compounds of formulae (Ib) and (II) are reacted in a solvent with said chlorinating agent in the presence of said base, optionally in the presence of a cyanide source.

9. The process as claimed in claim 8, where the solvent is selected from the group consisting of aprotic and dipolar aprotic solvents.

10. The process as claimed in claim 8, where the solvent is selected from the group consisting of ethyl acetate, propyl acetate, isopropyl acetate, butyl acetate, dichloromethane, dichloroethane, chlorotoluene, acetonitrile, butyronitrile and benzonitrile.

11. The process as claimed in claim 8, where the solvent is selected from the group consisting of ethyl acetate, dichloromethane and dichloroethane.

12. The process as claimed in claim 8, where the cyanide source is selected from the group consisting of acetone cyanohydrin and alkali metal cyanides.

13. The process as claimed in claim 8, where the cyanide source is acetone cyanohydrin.

* * * * *